United States Patent [19]

Törmälä et al.

[11] Patent Number: 4,743,257

[45] Date of Patent: May 10, 1988

[54] MATERIAL FOR OSTEOSYNTHESIS DEVICES

[75] Inventors: Pertti Törmälä, Tampere; Pentti Rokkanen, Helsinki; Juha Laiho; Markku Tamminmäki, both of Tampere; Seppo Vainionpää, Helsinki, all of Finland

[73] Assignee: Materials Consultants Oy, Tampere, Finland

[21] Appl. No.: 861,201

[22] Filed: May 8, 1986

[30] Foreign Application Priority Data

May 8, 1985 [FI] Finland ................................. 851828

[51] Int. Cl.$^4$ ................................. A61F 2/02; C08L 67/04
[52] U.S. Cl. ................................. 623/16; 264/257; 264/331.21; 623/66; 525/411; 525/415; 128/92 YR
[58] Field of Search ............... 523/113, 115, 116; 525/411, 415; 528/950; 623/16, 66; 264/257, 331.21

[56] References Cited

U.S. PATENT DOCUMENTS

| | | | |
|---|---|---|---|
| 2,703,316 | 3/1955 | Schneider | 260/78.3 |
| 3,297,033 | 1/1967 | Schmitt et al. | 128/335.5 |
| 3,739,773 | 6/1973 | Schmitt et al. | 128/92 BC |
| 3,839,297 | 10/1974 | Wasserman et al. | 260/78.3 R |
| 4,052,988 | 10/1977 | Doddi et al. | 128/335.5 |
| 4,263,185 | 4/1981 | Belykh et al. | 260/17.4 R |
| 4,279,249 | 7/1981 | Vert et al. | 128/92 D |
| 4,343,931 | 8/1982 | Barrows | 528/291 |
| 4,595,713 | 6/1986 | St. John | 525/415 X |

FOREIGN PATENT DOCUMENTS

| | | |
|---|---|---|
| 0146398 | 6/1985 | European Pat. Off. |
| 832405 | 6/1983 | Finland .................. 39/272 |
| PCT/US84/00104 | 1/1984 | PCT Int'l Appl. |
| 1034123 | 6/1966 | United Kingdom |

OTHER PUBLICATIONS

Kulkarni et al., J. Biomed. Mater. Res., 1971, 5, 169–181.
Vert et al., Makromol. Chem., Suppl., 1981, 5, 30–41.
Christel et al., Biomaterials, 1980, 271–280.
Tunc, Transactions of 9th Annual Meeting of the Society for Biomaterials, Birmingham, U.S.A., 1983, 47.

*Primary Examiner*—Earl Nielsen
*Attorney, Agent, or Firm*—Pollock, Vande Sande & Priddy

[57] ABSTRACT

Surgical osteosynthesis composite material, which is self-reinforced i.e. it is formed about the absorbable polymer or copolymer matrix which is reinforced with the absorbable reinforcement units which have the same chemical element percentage composition as the matrix has.

16 Claims, 1 Drawing Sheet

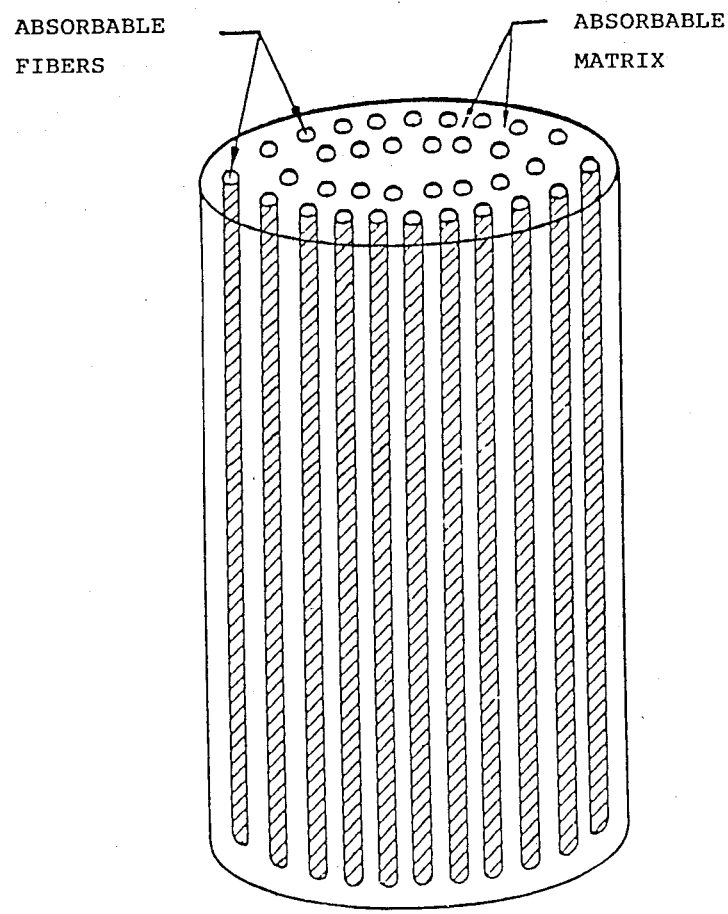

MATERIAL FOR OSTEOSYNTHESIS DEVICES

TECHNICAL FIELD

This invention relates to synthetic, polymeric surgical osteosynthesis composite material, which is absorbable (resorbable) in tissue without causing harmful tissue reactions. This material can be applied to manufacture osteosynthesis devices or their components plates, balks, rods, medullary nails, pins, screws or corresponding structures.

BACKGROUND ART

The manufacturing of osteosynthesis materials from absorbable polymers is known from several patents. The manufacturing of absorbable sutures and surgical elements from polyglycolide (PGA)

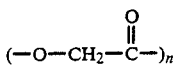   (I)

has been described in U.S. Pat. No. 3,297,033 and U.S. Pat. No. 3,739,773.

Sutures manufactured from polylactide (PLA)

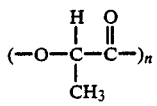   (II)

are described in U.S. Pat. No. 2,703,316.

Sutures manufactured from glycolide/lactide copolymers (PGA/PLA)

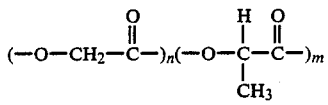   (III)

(where n and m are integers >1) are described in U.S. Pat. No. 3,839,297.

Sutures and osteosynthesis devices which are manufactured from poly-β-hydroxybutyric acid (PHB)

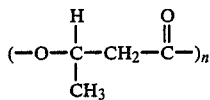   (IV)

are described in G.B. Pat. No. 1 034 123.

Sutures and osteosynthesis devices which are manufactured from polydioxanone (PDS)

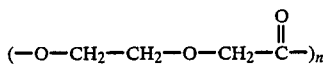   (V)

are described in U.S. Pat. No. 4,052,988.

Absorbable surgical devices which are manufactured from polyesteramides (PEA)

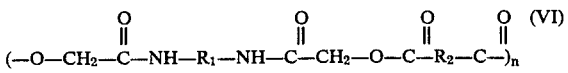   (VI)

are described in U.S. Pat. No. 4,343,931.

Absorbable surgical sutures and surgical devices, which are constructed of copolymer which contains units with the structural formula (VII)

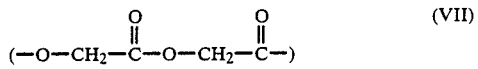   (VII)

as end sequences and the units with the formula (VII) combined randomly with the units (VIII)

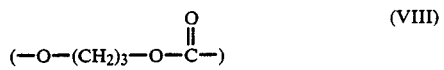   (VIII)

as middle sequence, are described in FI Pat. Appl. No. 83 2405.

Absorbable surgical devices of the above patents and patent applications are typically plates which are fixed to bones by screws, cylindrical medullary nails or corresponding structures which are manufactured by melting an absorbable polymer and by molding or pressing the melt into the suitable form. The mechanical strengths of such samples, which are manufactured by melt processing techniques, have typically the same order of magnitude as those of other similar synthetic polymers. Accordingly the tensile strengths of dry, unhydrolyzed samples manufactured about PBA, PLA, PHB and PGA/PLA have typically the order of magnitude of 40–80 MPa (see e.g. Kulkarni, R. K., Moore, E. G., Hegyeli, A. F. and Fred, L., *J. Biomed. Mater. Res.*, 1971, 5, 169, Vert, M., Chabot, F. and Leray, J., *Makromol. Chem., Suppl.* 1981, 5, 30, Christel, P., Chabot, F., Leray, J. L., Morin, C. and Vert, M., in Biomaterials (Eds. G. D. Winter, D. F. Gibbons and H. Plenk, Jr.), Wiley (1980), p. 271, Tunc, D. C., *Transactions of 9th Annual Meeting of the Society for Biomaterials*, Birmingham, USA, 1983, p. 47, Howells, E. R., *Chem. Ind.*, 1982, 7, 509).

The tensile strengths given above are modest when compared to the strengths of compact bone (ca. 80–200 MPa). Additionally melt processed homogeneous polymeric samples of the above polymers are in several cases brittle or too flexible to be used for bone surgical applications. Therefore the conventional applications of resorbable polymers in bone surgery have encountered severe difficulties.

The initial mechanical strength of surgical absorbable osteosynthesis materials has been improved.

For example, U.S. Pat. No. 4,279,249 suggests manufacturing composites consisting of a matrix of a lactic acid homopolymer, or a copolymer very high in lactic acid units and of discrete reinforcements (such as fibers, threads, films, tissues, plaits or poles) made of glycolic acid homopolymer or copolymers predominant in glycolic acid units. The mechanical strength of absorbable polymers has been increased also with bio-stable carbon fibers (J. Kilpikari, Lic. Thesis, Tampere Univ. of Technology, Tampere, Finland, 1985). In the case of known absorbable and partially absorbable composites the chemical element composition of the reinforcements differs from that of the matrix material and; therefore, the matrix and reinforcements cannot form, as a rule, strong chemical primary or secondary bonds with each other which leads to poor adhesion between material components.

Adhesion promoters, such as silanes or titanates etc., which are usually applied in polymeric reinforced composites, cannot be applied in surgical materials intended to be used in surgery because of their toxicity. Therefore good adhesion between matrix and reinforcement units of different chemical origin is difficult to achieve.

SUMMARY OF INVENTION

The invention is mainly characterized in that the osteosynthesis material is self-reinforced i.e. it is formed of an absorbable polymer or copolymer matrix which is reinforced with absorbable reinforcement which have the same chemical element percentage composition as does the matrix. It should be also noted that the matrix and reinforcement material which have the same chemical element percentage composition can be isomers, which means that the matrix and the reinforcement units have configurations which differ from each other.

The reinforcement embedded in the matrix can be in the form of fibers, threads, cords, twists, films, woven fabrics, ribbons, or corresponding structures.

BRIEF DESCRIPTION OF DRAWING

The FIGURE is a schematic diagram of the structure of the reinforced polymeric material of the present invention which is formed of absorbable polymeric matrix reinforced with the absorbable fibers having the same chemical element percentage composition as the matrix.

BEST AND VARIOUS MODES FOR CARRYING OUT THE INVENTION

The present invention relates to self-reinforced absorbable polymeric surgical osteosynthesis material, which is uniform in its chemical element structure and which therefore has good adhesion between the matrix and reinforcement elements. Therefore the material has excellent initial mechanical strength properties, such as high tensile, bending or shear strength and toughness, and therefore this material can be applied favorably as surgical absorbable osteosynthesis devices or as components or parts of such devices, such as osteosynthesis plates which are fixed to bones by screws, fixing screws, as medullary nails or as components (plates, rods or balks) of such osteosynthesis devices which are described in FI-patent No. 61402.

Self-reinforcement means that the polymeric matrix is reinforced with the reinforcement elements or materials (such as fibers) which have the same chemical element percentage composition as does the matrix. By applying self-reinforcement principle the high tensile strength (typically 500–900 MPa) of fibers can be effectively utilized, when manufacturing macroscopic samples. When strong oriented fiber structures are bound together with the polymer matrix which has the same chemical element composition as the fibers, the composite structure is obtained which has excellent adhesion between the matrix and reinforcement material and therefore also has excellent mechanical properties.

The annexed drawing shows schematically the structure of the material of this invention where the absorbable polymeric matrix is reinforced with the absorbable fibers.

The method is mainly characterized in that the part of the material which will form the matrix is subjected to heat and/or pressure in such a way that the physical condition of the part of material which will act as the matrix phase allows the development of adhesion between the nearby reinforcement units and the matrix.

There are alternative methods which can be applied in manufacturing of self-reinforced absorbable osteosynthesis materials of this invention. One method is to mix finely milled polymer powder with fibers, threads or corresponding reinforcement units which are manufactured of the same material or of its isomer with the same chemical element percentage composition and to heat the mixture under such conditions and using such temperatures that the finely milled particles are softened or melted but the reinforcement unit structures are not significantly softened or melted. When such composition is pressed to the suitable form the softened or melted particles form the matrix phase which binds the reinforcement units together and when this structure is cooled, a self-reinforced composite with excellent adhesion and mechanical properties is obtained.

The self-reinforced structure of the present invention is also obtained by combining together the melt of an absorbable polymer and fibers, threads or corresponding reinforcement elements of the same material, forming the mixture of the polymer melt and reinforcement elements into the desired form and cooling the formed polymer composite so rapidly that the reinforcement elements do not significantly lose their oriented internal structure.

One can also manufacture the self-reinforced absorbable material of the present invention by heating absorbable fibers, threads or corresponding structures in a pressurized mold under such circumstances that at least part of these structures are partially softened or melted on their surface. Under the pressure the softened or melted surface of fibers, threads or corresponding structures are coalesced together and when the mold is cooled, a self-reinforced composite structure is obtained. By a careful control of the heating conditions it is possible to process composite samples where the softened or melted surface regions of fibers, threads or corresponding units are very thin and, therefore, the portion of oriented fiber structure is very high leading to materials with high tensile, shear, bending and impact strength values.

The above manufacturing principles can be applied when the self-reinforced absorbable materials are manufactured by batch processes (such as compression molding and transfer molding) or by continuous processes (such as injection molding or extrusion or pultrusion).

Typical properties of the materials of this invention are the high content of oriented fibers bound together with thin matrix polymer layers between fibers, low porosity, smooth and compact surface, which properties are all obtained as a consequence of the application of pressure and possibly also of the heat during the manufacturing of the material. Good internal adhesion properties in combination with the above advantageous structural factors provide for the excellent mechanical strength properties such as high tensile, bending, compression or impact strength.

It is natural that the self-reinforced absorbable surgical material can include, in addition to the matrix and reinforcement polymers, auxiliary additives, such as colors, powder-like fillers or other additives.

The self-reinforced materials of the invention can be applied in osteosynthesis implants such as surgical devices or as their components in the form of plates, pins, nails, medullary rods, screws or in the form of other three-dimensional solids. The material can form also at least part of an osteosynthesis implant. It is natural that the at least partially absorbable matrix and/or reinforcement elements can contain additives such as colors, antioxidants, plasticizers, lubricants, fillers etc. which are desirable in processing of the material or to modify its properties or the properties of matrix and/or reinforcement elements.

When the self-reinforced material is applied as a part of a surgical plate, pin, rod etc. the self-reinforced structure may form e.g. the core of the device and the surface of the device can be prepared from other material. In this way the excellent mechanical properties of self-reinforced material can be combined with properties of other absorbable materials (such as slow absorption rate).

The self-reinforced material of the present invention can be applied also in several other ways in combination with other absorbable and/or biostable materials. Furthermore, the mechanical properties of the self-reinforced material can be modified by embedding into it absorbable reinforcing units with other hydrolytic properties than those of the self-reinforced material. Composites with excellent mechanical properties are also achieved when hybrid composites of self-reinforced materials with biostable fibers (such as carbon fibers) are manufactured.

The following non-limiting examples illustrate the present invention.

EXAMPLE 1

The melt of glycolide/lactide (90/10) copolymer (internal viscosity $|n|=1.5$ in 0.1% hexafluoroisopropanol solution (T=25° C.)) was mixed with the continuous fibers of the same material. The melt-fiber mixture was formed rapidly to cylindrical samples (diameter 4.5 mm) which were cooled rapidly and whose fiber content was 30% (w/w). The tensile strength of these self-reinforced absorbable composite rods was 260 MPa. The tensile strength of corresponding non-reinforced rods manufactured from glycolide/lactide copolymer melt was 50 MPa.

EXAMPLE 2

Glycolide/lactide copolymer sutures (Vicryl ®) (size 2 USP) were heated in vacuum at 185° C. for 6 min which caused the partial melting of fiber units of sutures. The material was compression molded into a cylindrical mold with a pressure of 2000 bar and it was cooled rapidly. The bending strength of these self-reinforced rods was 170 MPa. The bending strength of corresponding non-reinforced rods manufactured from glycolide/lactide copolymer melt was 90 MPa.

EXAMPLE 3

Polyglycolide sutures (Dexon ®) (size 2 USP) were heated in pressurized cylindrical mold (length 70 mm, diameter 4.5 mm) at 218° C. for 5 min with a pressure of 2000 bar. The softened fiber material was fused partially together and the mold was cooled to room temperature rapidly. The tensile strength of these self-reinforced absorbable composite rods was 380 MPa. The tensile strength of corresponding non-reinforced rods manufactured from polyglycolide melt was 60 MPa.

EXAMPLE 4

Polyglycolide sutures (Dexon ®) (size 2 USP) were melted at T=230° C. The polymer melt and corresponding continuous sutures (Dexon ®) were mixed rapidly together, formed to cylindrical rods (diameter 3.2 mm) and cooled rapidly. The fiber content of self-reinforced rods was 40% (w/w). Their tensile strength was 290 MPa. The tensile strength of corresponding non-reinforced rods manufactured from polyglycolide melt was 60 MPa.

EXAMPLE 5

Isomers which can be applied to manufacture absorbable osteosynthesis devices are e.g. isomers of polylactide like poly-L-lactide (PLLA) and the DL isomer (meso lactide). PLLA is crystalline polymer with a melting point of 180° C. and the DL isomer is an amorphous polymer. The self-reinforced material can be manufactured of these materials by combining DL isomer matrix and PLLA fiber, thread or corresponding reinforcement structures to each other by means of heat and pressure.

Bundles of poly-L-lactide (PLLA) fibers (fiber diameter 12 μm, amount of fibers in a slightly twisted bundle=200 pcs, molecular weight of PLLA=100,000) and the finely powdered DL isomer (meso lactide) (molecular weight=100,000) were mixed mechanically together and compression molded at 165° C. and 2000 bar pressure for 6 min and cooled rapidly. The fiber content of self-reinforced rods was 50% and their tensile strength was 300 MPa. Tensile strengths of non-reinforced rods manufactured from polymer melts were: PLLA 60 MPa and mesolactide 55 MPa.

EXAMPLE 6

Self-reinforced rods of EXAMPLE 3 were coated in an injection mold with 0.2 mm thick layer of poly-p-dioxanone melt ($|n|=0.8$ in 0.1% tetrachloroethane solution (T=25° C.), $T_m=110°$ C.) giving cylindrical, coated self-reinforced rods with the diameter of 4.9 mm. The bending strength of rods was 330 MPa. After hydrolysis of three weeks in distilled water (T=37° C.) the coated self-reinforced rods had the bending strength 160 MPa while the bending strength of non-coated self-reinforced rods was 90 MPa.

EXAMPLE 7

Poly-L-lactide ($M_w=100,000$) fibers (diameter 12 μm) were heated in pressurized cylindrical mold (length 70 mm, diameter 4.5 mm) at 180° C. for 7 min with a pressure of 2000 bar. The softened fiber material was fused partially together and the mold was cooled to room temperature rapidly. The tensile strength of these self-reinforced absorbable composite rods was 270 MPa. The tensile strength of corresponding non-reinforced rods manufactured from poly-L-lactide melt was 50 MPa.

EXAMPLE 8

Poly-β-hydroxybutyric acid ($M_w=80,000$) fibers (diameter 15 μm) were heated in pressurized cylindrical mold (length 70 mm, diameter 4.5 mm) at 175° C. for 5 min with a pressure of 2000 bar. The softened fiber material was fused partially together and the mold was cooled to room temperature rapidly. The tensile strength of these self-reinforced absorbable composite rods was 200 MPa. The tensile strength of corresponding non-reinforced rods manufactured from poly-β-hydroxybutyric acid melt was 40 MPa.

EXAMPLE 9

Polydioxanone sutures (PDS of Ethicon) (Size 0) were heated in pressurized cylindrical mold (length 70 mm, diameter 4.5 mm) at 103° C. for 6 min with a pressure of 2000 bar. The softened fiber material was fused partially together and the mold was cooled to room temperature rapidly. The shear strength of these self-reinforced absorbable composite rods was 140 MPa. The shear strength of corresponding non-reinforced rods manufactured from polydioxanone melt was 50 MPa.

EXAMPLE 10

Polyesteramide (with the chemical formula VI, where $R_1=R_2=-(CH_2)_{12}-$; $M_w=60,000$) fibers (diameter 12 µm) were heated in pressurized cylindrical mold (length 70 mm, diameter 4.5 mm) at 105° C. for 4 min with a pressure of 2000 bar. The softened fiber material was fused partially together and the mold was cooled to room temperature rapidly. The shear strength of these self-reinforced absorbable composite rods was 140 MPa. The shear strength of corresponding non-reinforced rods manufactured from polyesteramide melt was 50 MPa.

EXAMPLE 11

Polyglycolide sutures (Dexon ®) (Size 2) mixed with 10 wt-% of carbon fibers (with diameter 6 µm) were heated in pressurized cylindrical mold (length 70 mm, diameter 4.5 mm) at 218° C. for 5 min with a pressure of 2000 bar. The softened polyglycolide fiber material was fused partially together and the mould was cooled to room temperature rapidly. The tensile strength of this self-reinforced absorbable hybrid composite material containing carbon fibers was 450 MPa. The tensile strength of the corresponding carbon fiber reinforced material manufactured from polyglycolide melt-carbon fiber mixture was 160 MPa.

EXAMPLE 12

Glycolide/lactide copolymer sutures (Vicryl ®) containing 10 wt-% of polyglycolide sutures (Dexon ®) (Size 2) were heated in vacuum at 185° C. for 6 min which caused the partial melting of glycolide/lactide fiber units of Vicryl ® sutures. The material was compression moulded in a cylindrical mold (length 70 mm, diameter 4.5 mm) with a pressure of 2000 bar and it was cooled rapidly. A hybrid composite rod which was composed of self-reinforced glycolide/lactide material into which were embedded polyglycolide sutures was obtained. The bending strength of hybride composite material was 240 MPa. The bending strength of corresponding composite manufactured from glycolide/lactide copolymer melt reinforced with 10 wt-% of polyglycolide sutures was 150 MPa.

EXAMPLE 13

Monofilament sutures (size 0) manufactured from polyglycolide/trimethylenecarbonate copolymer (Maxon of Davis+Geck) were heated in a pressurized cylindrical mold (length 50 mm, diameter 3.2 mm) at 180° C. for 8 min with a pressure of 2000 bar. The sutures were partially fused together and the mold was cooled to room temperature rapidly. Self-reinforced absorbable rods with the shear strength of 110 MPa were obtained. The shear strength of corresponding non-reinforced rods manufactured from totally melted Maxon sutures was 60 MPa.

We claim:

1. Surgical, osteosynthesis composite material which is at least partially absorbable in living tissue characterized in that the osteosynthesis material comprises an absorbable polymer or copolymer matrix which is reinforced with absorbable polymeric reinforcement elements which have the same chemical element percentage composition as does the matrix.

2. Osteosynthesis composite material as claimed in claim 1, characterized in that the reinforcement elements are in the form of fibers, threads, twists, cords, films, ribbons, woven fabrics or corresponding material.

3. Osteosynthesis composite material as claimed in claim 1 characterized in that the absorbable matrix and reinforcement units are manufactured of polyglycolide or a glycolide copolymer.

4. Osteosynthesis composite material as claimed in claim 1 characterized in that the absorbable matrix and reinforcement units are manufactured of polylactide or a lactide copolymer.

5. Osteosynthesis composite material as claimed in claim 1 characterized in that the absorbable matrix and reinforcement units are manufactured of glycolide/lactide copolymer.

6. Osteosynthesis composite material as claimed in claim 1 characterized in that the absorbable matrix and reinforcement units are manufactured of poly-$\beta$-hydroxybutyric acid.

7. Osteosynthesis composite material as claimed in claim 1 characterized in that the absorbable matrix and reinforcement units are manufactured of polydioxanone.

8. Osteosynthesis composite material as claimed in claim 1 characterized in that the absorbable matrix and reinforcement units are manufactured of polyvinylalcohol.

9. Osteosynthesis composite material as claimed in claim 1 characterized in that the absorbable matrix and reinforcement units are manufactured of polyesteramide.

10. Osteosynthesis composite material as claimed in claim 1 characterized in that the material forms in the shape of a three-dimensional solid, an osteosynthesis implant, or at least part of an osteosynthesis implant.

11. The osteosynthesis composite material of claim 10 wherein said implant is in the form of a plate, pin, nail, medullary rod, screw, or balk.

12. A method for manufacturing material for the osteosynthesis devices of any of claims 1-10 which comprises mixing together a melt of the absorbable polymer or copolymer said melt formed by heat and/or pressure, and the absorbable reinforcement elements to provide a mixture and forming the mixture into the desired shape and permitting the shape to cool down.

13. The method of claim 12 wherein said reinforcement element is in the form of fiber, thread, twist, cord, film, ribbon, or woven fabric.

14. The method of claim 12 wherein the part of the material which will form the matrix is subjected to heat and/or pressure in such a way that the physical condition of the part of the material which will act as the matrix phase allows the development of adhesion between the nearly reinforcement elements and the matrix.

15. The method of claim 14 wherein the absorbable reinforcement element is heated in such a way that the material is softened or melted and coalesced at least partially and the material is formed into the desired shape by means of pressure.

16. The method of claim 12 wherein the absorbable reinforcement element is heated in such a way that the material is softened or melted and coalesced at least partially and the material is formed into the desired shape by means of pressure.

* * * * *

UNITED STATES PATENT AND TRADEMARK OFFICE
CERTIFICATE OF CORRECTION

PATENT NO. : 4,743,257

DATED : May 10, 1988

INVENTOR(S) : Pertti Tormala, et al.

It is certified that error appears in the above-identified patent and that said Letters Patent is hereby corrected as shown below:

Column 3, line 16 please change the word "units" to --- elements ---.

Column 8, line 9 please change the word "units" to --- elements ---.

Column 8, line 13 please change the word "units" to --- elements ---.

Column 8, line 17 please change the word "units" to --- elements ---.

Column 8, line 21 please change the word "units" to --- elements ---.

Column 8, line 25 please change the word "units" to --- elements ---.

Column 8, line 29 please change the word "units" to --- elements ---.

Column 8, line 33 please change the word "units" to --- elements ---.

Column 8, line 57 please change the word "nearly" to --- nearby ---.

Signed and Sealed this

Fourth Day of December, 1990

*Attest:*

HARRY F. MANBECK, JR.

*Attesting Officer*   *Commissioner of Patents and Trademarks*

(12) REEXAMINATION CERTIFICATE (4581st)
United States Patent
Törmälä et al.

(10) Number: US 4,743,257 C1
(45) Certificate Issued: May 28, 2002

(54) MATERIAL FOR OSTEOSYNTHESIS DEVICES

(75) Inventors: Perti Törmälä, Tampere; Pentti Rokkanen, Helsinki; Juha Laiho; Markku Tamminmäki, both of Tampere; Seppo Vainionpää, Helsinki, all of (FI)

(73) Assignee: Materials Consultants Oy, Tampere (FI)

Reexamination Request:
No. 90/004,677, Jun. 25, 1997

Reexamination Certificate for:
Patent No.: 4,743,257
Issued: May 10, 1988
Appl. No.: 06/861,201
Filed: May 8, 1986

Certificate of Correction issued Dec. 4, 1990.

(30) Foreign Application Priority Data

May 8, 1985 (FI) ............................................. 851828

(51) Int. Cl.$^7$ ........................................... A61F 2/28
(52) U.S. Cl. ............................... 623/23.58; 264/257
(58) Field of Search ..................... 623/23.58; 264/257

(56) References Cited

U.S. PATENT DOCUMENTS

| | | | | |
|---|---|---|---|---|
| 2,703,316 A | * | 3/1955 | Schneider | 260/78.3 |
| 3,297,033 A | * | 1/1967 | Schmitt et al. | 128/335.5 |
| 3,463,158 A | * | 8/1969 | Schmitt et al. | 606/154 |
| 3,739,773 A | * | 6/1973 | Schmitt et al. | 128/92 BC |
| 3,839,297 A | * | 10/1974 | Wasserman et al. | 260/78.3 R |
| 4,052,988 A | * | 10/1977 | Doddi et al. | 128/335.5 |
| 4,263,185 A | * | 4/1981 | Belykh et al. | 260/17.4 R |
| 4,279,249 A | * | 7/1981 | Vert et al. | 128/92 D |
| 4,343,931 A | * | 8/1982 | Barrows | 528/291 |
| 4,595,713 A | * | 6/1986 | St. John | 523/105 |
| 4,655,203 A | * | 4/1987 | Tormala et al. | 623/16 |

FOREIGN PATENT DOCUMENTS

| | | |
|---|---|---|
| EP | 0 011 528 B1 | 5/1980 |
| EP | 0 011 528 A1 | 5/1980 |
| EP | 0146398 | * 6/1985 |
| GB | 1034123 | * 6/1966 |
| WO | 84/03035 | * 8/1984 |

OTHER PUBLICATIONS

Ian van Randenborgh, "Biodegenerable Implantate am Knochen—Idee, Raalität und Zukunft?", Universität Würzburg, Nov. 1983.
A.N. Antonov and L.P. Mikhailova, "Study of Production of Self–Reinforced and Self–Bonding Materials (SRM)," Journal of Applied Chemistry USSR, vol. 42 (1969), pp. 1788–1791.
Kulkarni et al, "Biodegradable Poly (lactic acid) Polymers", J. Biomed. Mater. Res., vol. 5, pp. 169–181, (1971).*
Vert et al, "Stereoregular Bioresorbable Polyesters For Orthopedic Surgery" Makromol. Chem., Suppl., vol. 5, pp. 30–41, (1981).*
Christel et al, "Biodegradable Composites For Internal Fixation", Biomaterials, pp. 271–280, (1980).*
Tunc, "A High Strength Absorbable Polymer For Internal Bone Fixation", Transaction of 9th Annual Meeting of the Society of Biomaterials, Birmingham, USA, p. 47, (1983).*
Dr. Günther Goldbach, et al., Ullman's Encyclopedia of Technical Chemistry, Plastics, States of Order and Properties, 4th Edition, Weinheim, 1978.

* cited by examiner

Primary Examiner—Paul Prebilic

(57) ABSTRACT

Surgical osteosynthesis composite material, which is self-reinforced i.e. it is formed about the absorbable polymer or copolymer matrix which is reinforced with the absorbable reinforcement units which have the same chemical element percentage composition as the matrix has.

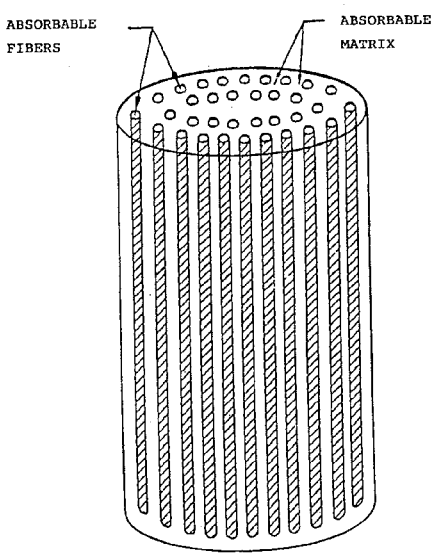

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8, 10 and 12–16 are cancelled.

Claims 1–7, 9 and 11 are determined to be patentable as amended.

New claims 17–19 are added and determined to be patentable.

1. [Surgical] *A surgical,* osteosynthesis composite material which is at least partially absorbable in living tissue [characterized in that], *wherein the osteosynthesis material* comprises an absorbable polymer or copolymer matrix which is reinforced with absorbable polymeric reinforcement elements [which], *wherein the reinforcement elements have the same chemical element percentage composition as* [does] the matrix, *said composite material having an initial shear strength of 110 to 140 MPa, or an initial tensile strength of 200 to 450 MPa or an initial bending strength of 240 to 330 MPa, resulting from the matrix being reinforced with the reinforcement elements.*

2. [Osteosynthesis] *The* composite material [as claimed in] *of* claim 1, [characterized in that the] *wherein said* reinforcement elements [are in] *have* the form of fibers, threads, twists, cords, films, ribbons, woven fabrics or *any* corresponding [material] *form of said reinforcement elements*.

3. [Osteosynthesis] *The* composite material [as claimed in] *of* claim 1, [characterized in that] *wherein* the absorbable matrix and reinforcement elements are [manufactured] *each comprised* of polyglycolide or a glycolide copolymer.

4. [Osteosynthesis] *The* composite material [as claimed in] *of* claim 1, [characterized in that] *wherein* the absorbable matrix and reinforcement elements are [manufactured] *each comprised* of polylactide or a lactide copolymer.

5. [Osteosynthesis] *The* composite material [as claimed in] *of* claim 1 [characterized in that], *wherein* the absorbable matrix and reinforcement elements are [manufactured] *each comprised* of glycolide/lactide copolymer.

6. [Osteosynthesis] *The* composite material [as claimed in] *of* claim 1 [characterized in that], *wherein* the absorbable matrix and reinforcement elements are [manufactured] *each comprised* of poly-β-hydroxybutyric acid.

7. [Osteosynthesis] *The* composite material [as claimed in] *of* claim 1 [characterized in that], *wherein* the absorbable matrix and reinforcement elements are [manufactured] *each comprised* of polydioxanone.

9. [Osteosynthesis] *The* composite material [as claimed in] *of* claim 1 [characterized in that], *wherein* the absorbable matrix and reinforcement elements are [manufactured] *each comprised* of polyesteramide.

11. The [osteosynthesis] composite material of claim [10] *1, wherein said material is formed into an* implant [is] in the form of a plate, pin, nail, medullary rod, screw or balk.

*17. A method for manufacturing the composite material according to any of claims 1–7, 9 and 11 comprising the steps of:*

*mixing said reinforcement elements in a mold with a melt of said absorbable polymer or copolymer matrix, wherein said mold is pressurized and has a shape that corresponds to the desired shape of said composite material;*

*subjecting said absorbable polymeric reinforcement elements and said matrix to heat and pressure in the mold to form said absorbable polymeric reinforcement elements and said matrix into said desired shape; and*

*rapidly cooling the mold and the composite material.*

*18. A method according to claim 17 wherein the step of heating said reinforcement elements and said matrix comprises the step of at least partially melting at least some of said reinforcement elements to form at least a part of said matrix.*

*19. A surgical, osteosynthesis composite material which is at least partially absorbable in living tissue, wherein the osteosynthesis material comprises an absorbable polymer of copolymer matrix which is reinforced with absorbable polymeric reinforcement elements, wherein the reinforcement elements have the same chemical element percentage composition as the matrix, said composite material having a percent fiber content of at least 30%.*

* * * * *